(12) United States Patent
Mastrototaro

(10) Patent No.: US 7,785,313 B2
(45) Date of Patent: Aug. 31, 2010

(54) CLOSED LOOP/SEMI-CLOSED LOOP THERAPY MODIFICATION SYSTEM

(75) Inventor: John J. Mastrototaro, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 48 days.

(21) Appl. No.: 12/174,552

(22) Filed: Jul. 16, 2008

(65) Prior Publication Data

US 2008/0275384 A1 Nov. 6, 2008

Related U.S. Application Data

(63) Continuation of application No. 12/146,340, filed on Jun. 25, 2008, which is a continuation-in-part of application No. 11/739,927, filed on Apr. 25, 2007.

(60) Provisional application No. 60/957,957, filed on Aug. 24, 2007, provisional application No. 60/950,779, filed on Jul. 19, 2007.

(51) Int. Cl.
*A61M 31/00* (2006.01)

(52) U.S. Cl. .................................. 604/503; 604/66
(58) Field of Classification Search .............. 604/890.1, 604/503, 504, 65–67
See application file for complete search history.

(56) References Cited

U.S. PATENT DOCUMENTS

| | | | |
|---|---|---|---|
| 6,379,301 B1 * | 4/2002 | Worthington et al. | 600/309 |
| 6,427,088 B1 * | 7/2002 | Bowman et al. | 607/60 |
| 2006/0020188 A1 * | 1/2006 | Kamath et al. | 600/345 |

* cited by examiner

*Primary Examiner*—Kevin C Sirmons
*Assistant Examiner*—Bradley J Osinski

(57) ABSTRACT

A closed loop/semi-closed loop infusion system provides therapy modification and safeguards against the over-delivery or under-delivery of insulin. A glucose sensor system is configured to obtain a measured blood glucose value. A controller is operationally connected with the glucose sensor system and configured to trigger an alarm based on a measured blood glucose value or amount of insulin delivered, selectively perform calibration of the glucose sensor system when the alarm is triggered, and adjust a therapy delivery parameter when the alarm is triggered, wherein the adjusted therapy delivery parameter is limited to be within a boundary. Thereafter, a delivery system delivers therapy at the adjusted therapy delivery parameter.

24 Claims, 11 Drawing Sheets

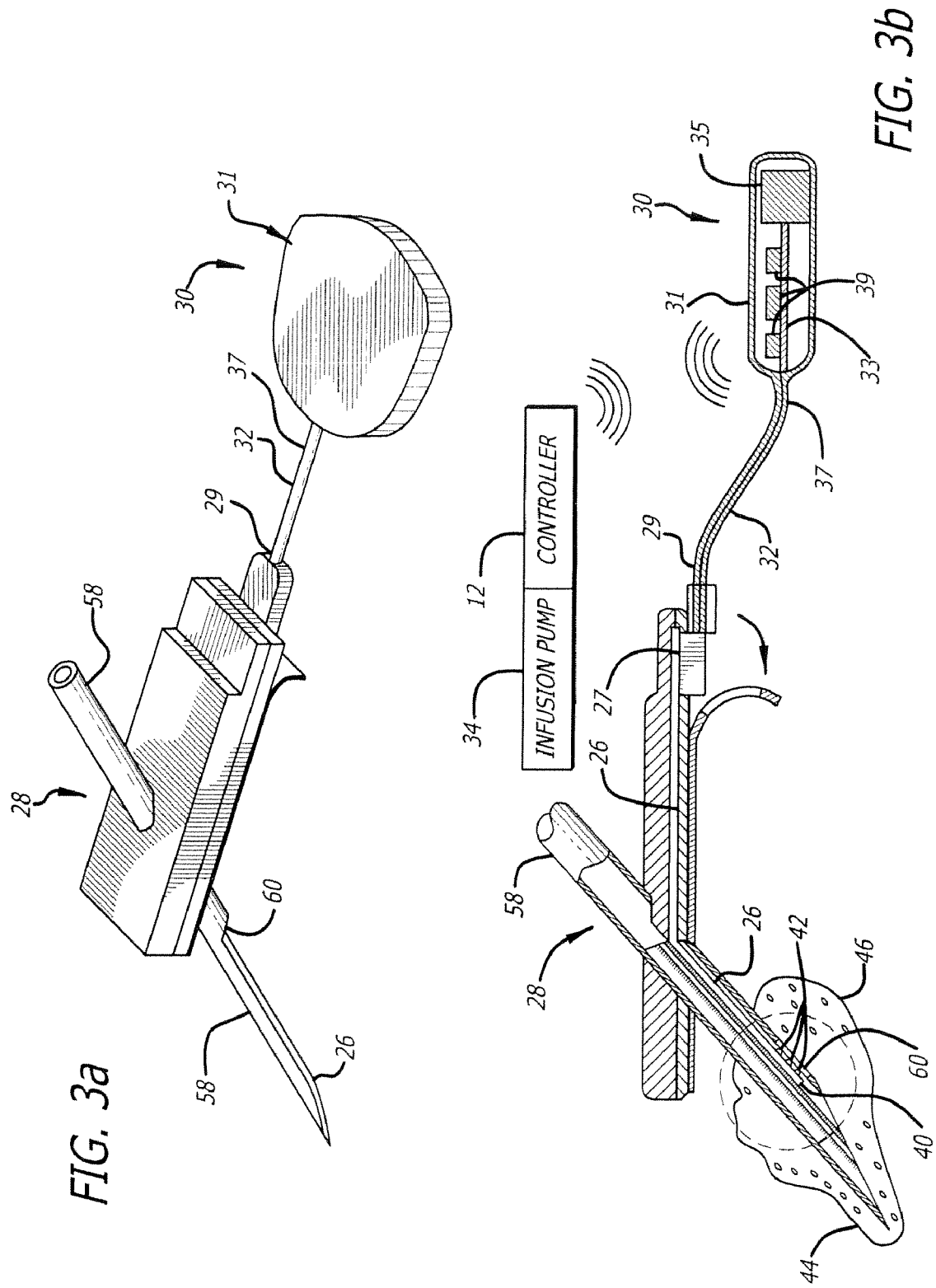

CLOSED LOOP/SEMI-CLOSED LOOP THERAPY MODIFICATION SYSTEM

CROSS-REFERENCE TO RELATED APPLICATIONS

This application is a continuation of U.S. patent application Ser. No. 12/146,340, filed Jun. 25, 2008, which is a continuation-in-part of U.S. patent application Ser. No. 11/739,927, filed Apr. 25, 2007, and entitled "Closed Loop/Semi-Closed Loop Therapy Modification System," which are herein incorporated by reference in their entirety. This application further claims the benefit and right of priority to U.S. provisional application Ser. No. 60/950,779, filed on Jul. 19, 2007 and U.S. provisional application Ser. No. 60/957,957, filed on Aug. 24, 2007, the contents of which are herein incorporated by reference in their entirety.

FIELD

This invention is directed to infusion systems in closed loop or semi-closed loop applications and more specifically to systems for countering the over/under delivery of medication by selectively performing calibration of a glucose sensor system when an alarm is triggered based on a measured blood glucose value or amount of insulin delivered.

BACKGROUND

Diabetes mellitus is the most common of endocrine disorders, and is characterized by inadequate insulin action. Diabetes mellitus has two principal variants, known as Type 1 diabetes and Type 2 diabetes. The latter is also referred to as DM/II (diabetes mellitus type 2), adult-onset diabetes, maturity-onset diabetes, or NIDDM (non-insulin dependent diabetes mellitus).

In the body, most carbohydrates are converted into glucose, which is then absorbed into the bloodstream. Therefore, eating carbohydrates usually makes blood sugar levels increase. As the glucose level increases in the blood, the pancreas releases an insulin hormone. Insulin is necessary to transfer glucose from the blood into the cells and use the glucose as an energy source in the cells.

However, in people with diabetes, the pancreas does not make enough insulin (Type 1 diabetes) or the body cannot respond normally to the released insulin (Type 2 diabetes). In both types of diabetes, glucose cannot absorb into the cells normally, thus causing a person's blood sugar level to increase excessively. Therefore, people with diabetes may keep track of their carbohydrate intake to be able to expect or predict increased levels of blood glucose when they have ingested foods containing carbohydrates.

Over the years, body characteristics have been determined by obtaining a sample of bodily fluid. For example, diabetics often test for blood glucose levels. Traditional blood glucose determinations have utilized a finger prick method using a lancet to withdraw a small blood sample. These systems are designed to provide data at discrete points but do not provide continuous data to show variations in the characteristic between testing times. These discrete measurements are capable of informing a patient the state of his blood glucose values at a point in time. Thus, the patient has enough information to administer "correction" amounts of insulin to reduce his current blood glucose reading. However, these discrete readings are not able to provide enough information for any type of automatic or semi-automatic system of administering insulin based on blood glucose values.

Recently, a variety of implantable electrochemical sensors have been developed for detecting and/or quantifying specific agents or compositions in a patient's blood or interstitial fluid. For instance, glucose sensors are being developed for use in obtaining an indication of blood glucose levels in a diabetic patient. These glucose sensors connected (wired or wirelessly) to a blood glucose monitor can provide continuous glucose readings over a period of time, such as 3 to 5 days. Such readings are useful in monitoring and/or adjusting a treatment regimen which typically includes the regular administration of insulin to the patient.

Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571. In addition, characteristic glucose monitors used to provide continuous glucose data are described in commonly assigned U.S. patent application Ser. No. 11/322,568 entitled "Telemetered Characteristic Monitor System and Method of Using the Same" filed on Dec. 30, 2005, which is herein incorporated by reference in its entirety. In addition, infusion pumps receiving sensor data are described in commonly assigned U.S. patent application Ser. No. 10/867,529 entitled "System for Providing Blood Glucose Measurements to an Infusion Device" filed on Oct. 14, 2004, which is herein incorporated by reference in its entirety.

As sensor technology improves, there is greater desire to use the sensor values to control the infusion of drugs and medicine, such as insulin in a closed loop or semi-closed loop system. Specifically, a closed loop system for diabetes entails a glucose sensor and an insulin infusion pump attached to a patient, wherein the delivery of insulin is automatically administered by a controller of the infusion pump based on the sensor's glucose value readings. A semi-closed system typically includes a patient intervention step, wherein the amount of insulin to be infused as calculated by the controller of the infusion pump requires patient acceptance before delivery.

However, given the ramifications of over-delivery and/or under-delivery of medication, there has yet to be developed a working closed loop/semi-closed loop system that establishes sufficient safeguards for countering the over-delivery and/or under-delivery of insulin. In addition, there has yet to be developed a working closed loop/semi-closed loop system providing robust real-time calibration adjustment procedures which allows a patient to forgo calibration as needed.

SUMMARY

According to an embodiment of the invention, a closed loop/semi-closed loop infusion system and method for providing intelligent therapy modification is described. Embodiments of the present invention include triggering an alarm based on a measured blood glucose value or amount of insulin delivered. In preferred embodiments, the method selectively performs calibration of a glucose sensor system when the alarm is triggered, and adjusts a therapy delivery parameter when the alarm is triggered, wherein the adjusted therapy delivery parameter is limited to be within a boundary. Thereafter, therapy is delivered at the adjusted therapy delivery parameter.

In one embodiment, the alarm is triggered when the measured blood glucose value is not consistent with a target blood glucose value. Alternatively, the alarm is triggered when the amount of insulin delivered is not consistent with an expected amount of delivered insulin.

In one embodiment, selectively performing calibration of the glucose sensor system includes informing a user that calibration needs to be performed, prompting the user to decide whether the calibration is to be performed, performing the calibration if the user decides to perform the calibration, and proceeding to adjust the therapy delivery parameter if the user decides not to perform the calibration.

Preferably, the therapy delivery parameter is adjusted according to a default basal pattern if the user decides not to perform the calibration. In one embodiment, adjusting the therapy delivery parameter comprises suspending closed-loop therapy delivery, and reverting to open-loop therapy delivery using the default basal pattern. Afterward, closed-loop therapy delivery may be resumed if a condition triggering the alarm is corrected. Otherwise, open-loop therapy delivery may be continued if the condition triggering the alarm is not corrected.

Preferably, the method further comprises obtaining a measured blood glucose value after performing the calibration, and comparing the measured blood glucose value to a target blood glucose value. Alternatively, the method further comprises determining that a calibrated measured blood glucose value is not consistent with a target blood glucose value after performing the calibration, and proceeding to adjust the therapy delivery parameter if the calibrated measured blood glucose value is not consistent with the target blood glucose value. In one embodiment, the method further comprises proceeding to adjust the therapy delivery parameter if the user decides to perform the calibration at a later time.

Preferably, the method further comprises prompting a patient to accept the adjusted therapy delivery parameter prior to delivering the therapy. Preferably, the method further comprises performing a safety action if the adjusted therapy delivery parameter exceeds the boundary. Preferably, the therapy delivery parameter is a basal rate.

Preferably, the method further comprises logging the adjusted therapy delivery parameter. Preferably, selectively performing calibration of the glucose sensor system further comprises obtaining a calibration value from a glucose meter.

In one embodiment, the boundary comprises 25% above or below a preset basal rate. In another embodiment, the boundary comprises a maximum allowed increase or decrease of a preset basal rate. In an alternative embodiment, an absolute value of the maximum allowed increase does not equal an absolute value of the maximum allowed decrease.

According to another embodiment of the invention, the system comprises a glucose sensor system and a controller operationally connected with the glucose sensor system. In preferred embodiments, the controller triggers an alarm based on a measured blood glucose value or amount of insulin delivered, selectively performs calibration of the glucose sensor system when the alarm is triggered, and adjusts a therapy delivery parameter when the alarm is triggered, wherein the adjusted therapy delivery parameter is limited to be within a boundary.

Preferably, the system further comprises a delivery system operationally connected with the controller and configured to deliver therapy at the adjusted therapy delivery parameter. In one embodiment, the controller triggers the alarm when the measured blood glucose value is not consistent with a target blood glucose value. Alternatively, the controller triggers the alarm when the amount of insulin delivered is not consistent with an expected amount of delivered insulin.

In one embodiment, the controller selectively performing calibration of the glucose sensor system includes informing a user that calibration needs to be performed, prompting the user to decide whether the calibration is to be performed, performing the calibration if the user decides to perform the calibration, and proceeding to adjust the therapy delivery parameter if the user decides not to perform the calibration.

Preferably, the controller adjusts the therapy delivery parameter according to a default basal pattern if the user decides not to perform the calibration. In one embodiment, the controller adjusts the therapy delivery parameter by suspending closed-loop therapy delivery, and reverting to open-loop therapy delivery using the default basal pattern. Afterward, closed-loop therapy delivery may be resumed if a condition triggering the alarm is corrected. Otherwise, open-loop therapy delivery may be continued if the condition triggering the alarm is not corrected.

Preferably, the controller obtains a measured blood glucose value after performing the calibration, and compares the measured blood glucose value to a target blood glucose value. Alternatively, the controller determines that a calibrated measured blood glucose value is not consistent with a target blood glucose value after performing the calibration, and proceeds to adjust the therapy delivery parameter if the calibrated measured blood glucose value is not consistent with the target blood glucose value. In one embodiment, the controller proceeds to adjust the therapy delivery parameter if the user decides to perform the calibration at a later time.

Preferably, the controller prompts a patient to accept the adjusted therapy delivery parameter prior to delivering the therapy. Preferably, the therapy delivery parameter is a basal rate. Preferably, the controller logs the adjusted therapy delivery parameter. Preferably, selectively performing calibration of the glucose sensor system further comprises obtaining a calibration value from a glucose meter.

In one embodiment, the boundary comprises 25% above or below a preset basal rate. In another embodiment, the boundary comprises a maximum allowed increase or decrease of a preset basal rate. In an alternative embodiment, an absolute value of the maximum allowed increase does not equal an absolute value of the maximum allowed decrease.

According to another embodiment of the invention, the system comprises means for triggering an alarm based on a measured blood glucose value or amount of insulin delivered. The system also comprises means for selectively performing calibration of a glucose sensor system when the alarm is triggered, and means for adjusting a therapy delivery parameter when the alarm is triggered, wherein the adjusted therapy delivery parameter is limited to be within a boundary. The system further comprises means for delivering therapy at the adjusted therapy delivery parameter.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 3(a) is a perspective view of a glucose sensor system for use in an embodiment of the present invention.

FIG. 3(b) is a side cross-sectional view of the glucose sensor system of FIG. 3(a).

DETAILED DESCRIPTION

Figure 1:
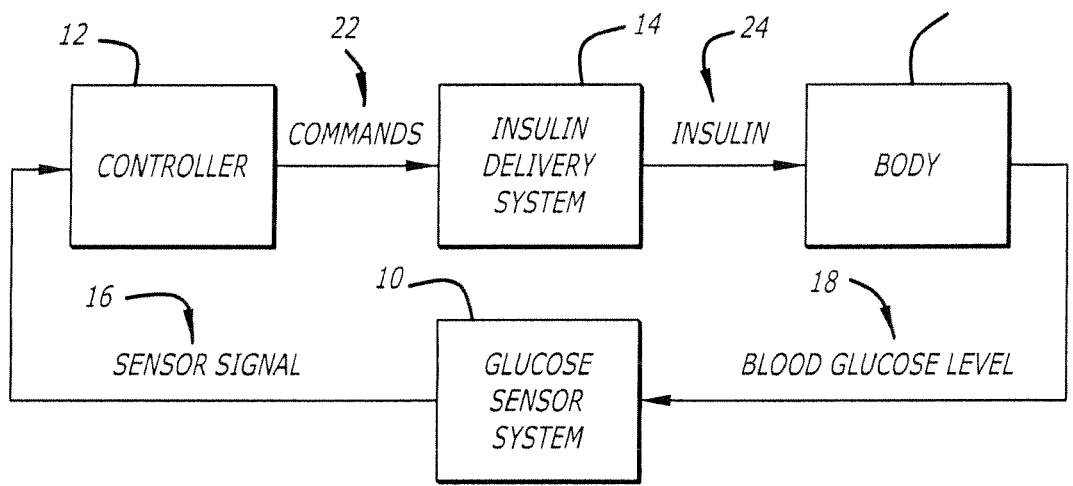
FIG. 1 is a block diagram of a closed loop glucose control system in accordance with an embodiment of the present invention.

As shown in the drawings for purposes of illustration, the invention is embodied in a closed loop/semi-closed infusion system for regulating the rate of fluid infusion into a body of a user based on feedback from an analyte concentration measurement taken from the body. In particular embodiments, the invention is embodied in a control system for regulating the rate of insulin infusion into the body of a user based on a glucose concentration measurement taken from the body.

The system is preferably designed to model a pancreatic beta cell (β-cell). In other words, the system controls an infusion device to release insulin into a body of a user in a similar concentration profile as would be created by fully functioning human β-cells when responding to changes in blood glucose concentrations in the body.

Thus, the system simulates the body's natural insulin response to blood glucose levels and not only makes efficient use of insulin, but also accounts for other bodily functions as well since insulin has both metabolic and mitogenic effects. However, algorithms used must model the β-cells closely. Because the algorithms are designed to minimize glucose excursions in the body, without regard for how much insulin is delivered, the algorithms may cause excessive weight gain, hypertension, and atherosclerosis.

In preferred embodiments of the present invention, the system is intended to emulate the in vivo insulin secretion pattern and to adjust this pattern consistent with the in vivo β-cell adaptation experienced by normal healthy individuals. The in vivo β-cell response in subjects with normal glucose tolerance (NGT), with widely varying insulin sensitivity ($S_I$), is the optimal insulin response for the maintenance of glucose homeostasis.

The preferred embodiments of the present invention include a glucose sensor system 10, a controller 12 and an insulin delivery system 14, as shown in FIG. 1. The glucose sensor system 10 generates a sensor signal 16 representative of blood glucose levels 18 in the body 20, and provides the sensor signal 16 to the controller 12. The controller 12 receives the sensor signal 16 and generates commands 22 that are communicated to the insulin delivery system 14. The insulin delivery system 14 receives the commands 22 and infuses insulin 24 into the body 20 in response to the commands 22. In an alternative semi-closed loop embodiment, the commands 22 would have to be confirmed by the user before the insulin delivery system 14 would infuse insulin.

Generally, the glucose sensor system 10 includes a glucose sensor, sensor electrical components to provide power to the sensor and generate the sensor signal 16, a sensor communication system to carry the sensor signal 16 to the controller 12, and a sensor system housing for the electrical components and the sensor communication system.

Typically, the controller 12 includes controller electrical components and software to generate commands for the insulin delivery system 14 based on the sensor signal 16, and a controller communication system to receive the sensor signal 16 and carry commands to the insulin delivery system 14.

The insulin delivery system 14 preferably includes an infusion device and an infusion tube to infuse insulin 24 into the body 20. For example, the infusion device includes infusion electrical components to activate an infusion motor according to the commands 22, an infusion communication system to receive the commands 22 from the controller 12, and an infusion device housing to hold the infusion device.

In preferred embodiments, the controller 12 is housed in the infusion device housing and the infusion communication system is an electrical trace or a wire that carries the commands 22 from the controller 12 to the infusion device. In alternative embodiments, the controller 12 is housed in the sensor system housing and the sensor communication system is an electrical trace or a wire that carries the sensor signal 16 from the sensor electrical components to the controller electrical components. In other alternative embodiments, the controller 12 has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces.

Figure 2:
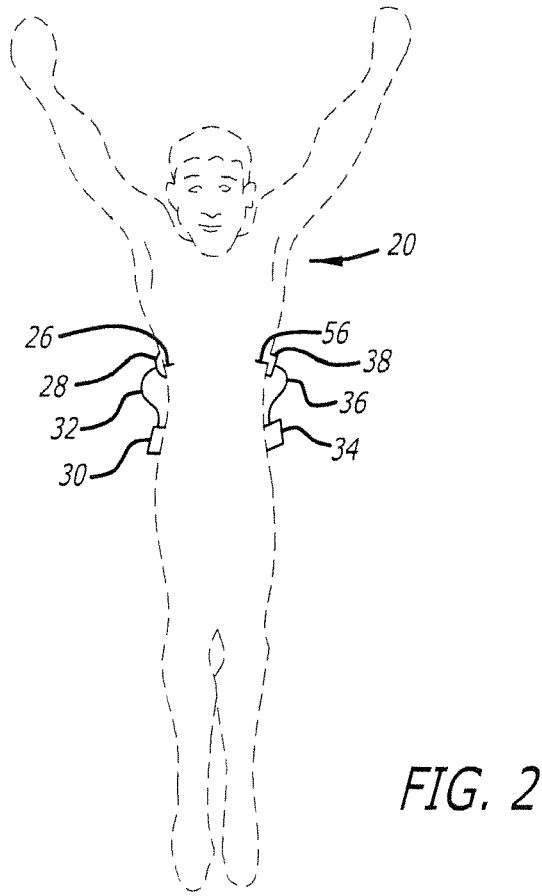
FIG. 2 is a front view of a closed loop system located on a body in accordance with an embodiment of the present invention.
Figure 3C:
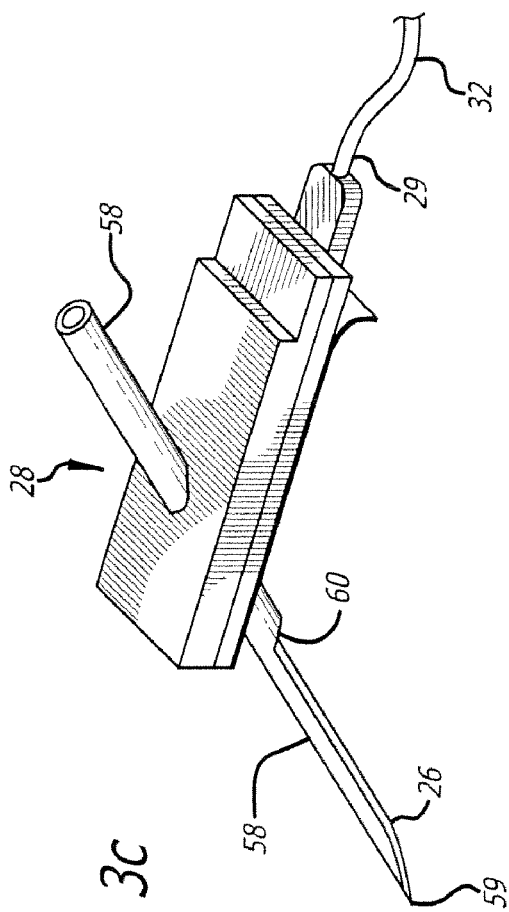
FIG. 3(c) is a perspective view of a sensor set of the glucose sensor system of FIG. 3(a) for use in an embodiment of the present invention.
Figure 3D:
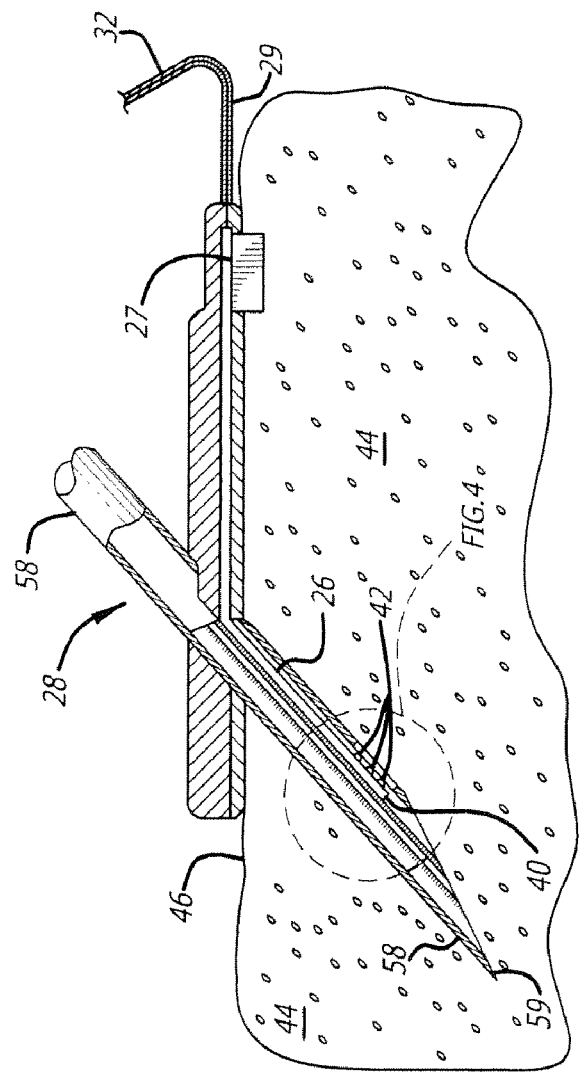
FIG. 3(d) is a side cross-sectional view of the sensor set of FIG. 3(c).
Figure 4:
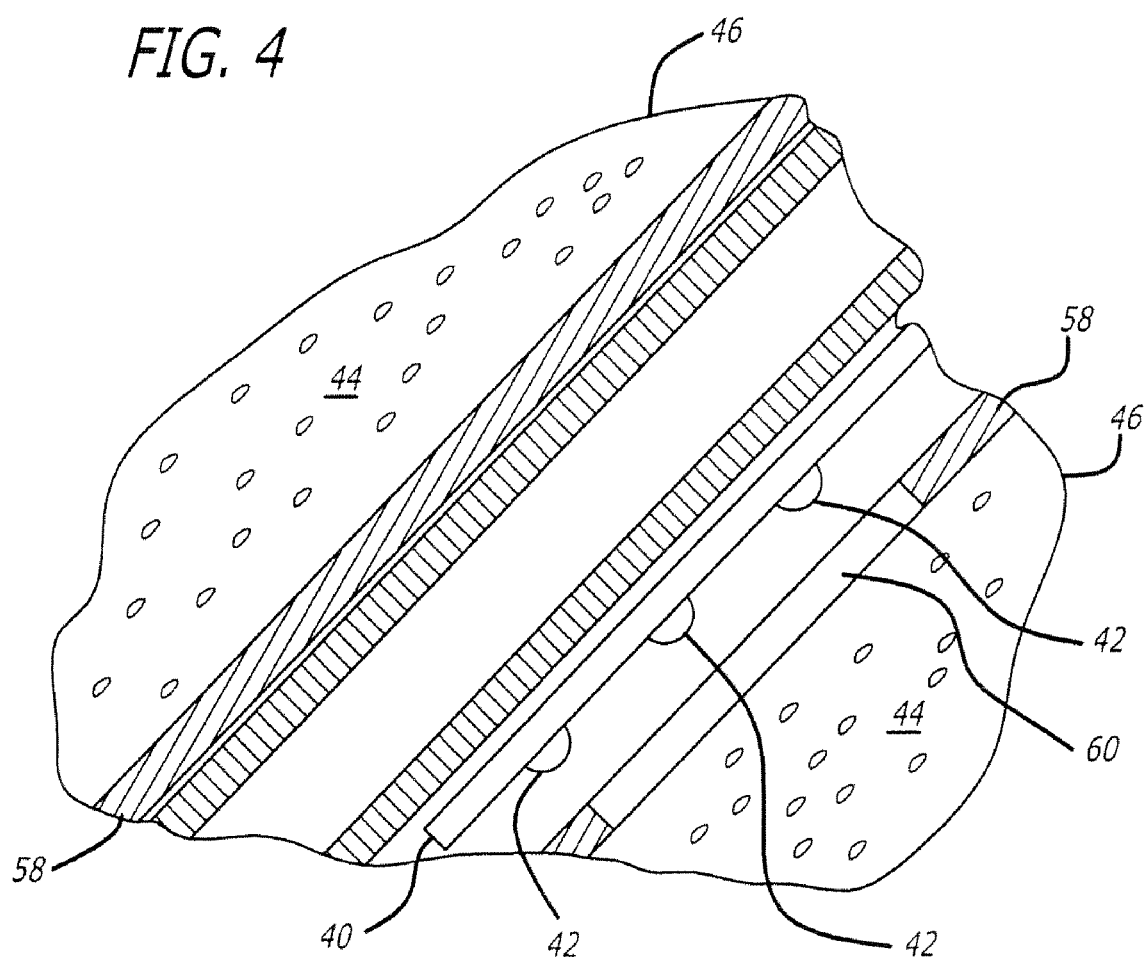
FIG. 4 is a cross sectional view of a sensing end of the sensor of FIG. 3(d).

FIG. 2 is a front view of a closed loop system located on a body in accordance with an embodiment of the present invention. Referring to FIG. 2, the closed loop system includes a sensor set 26, a sensor set 28, a telemetered characteristic monitor transmitter 30, a sensor cable 32, an infusion pump 34, an infusion tube 36, and an infusion set 38, all worn on the body 20 of a user. Referring to FIGS. 3(a) and 3(b), the telemetered characteristic monitor transmitter 30 includes a transmitter housing 31 that supports a printed circuit board 33, batteries 35, antenna (not shown), and a sensor cable connector (not shown). Referring to FIGS. 3(b), 3(d) and 4, a sensing end 40 of the sensor 26 has exposed electrodes 42 and is inserted through skin 46 into a subcutaneous tissue 44 of a user's body 20. The electrodes 42 are in contact with interstitial fluid (ISF) that is present throughout the subcutaneous tissue 44. Referring to FIGS. 3(b) and 3(d), the sensor 26 is held in place by the sensor set 28, which is adhesively secured to the user's skin 46. The sensor set 28 provides for a connector end 27 of the sensor 26 to connect to a first end 29 of the sensor cable 32. A second end 37 of the sensor cable 32 connects to the transmitter housing 31. The batteries 35 included in the transmitter housing 31 provide power for the sensor 26 and electrical components 39 on the printed circuit board 33. The electrical components 39 sample the sensor signal 16 and store digital sensor values (Dsig) in a memory and then periodically transmit the digital sensor values Dsig from the memory to the controller 12, which is included in the infusion device.

As shown in FIGS. 3(a)-3(d), the telemetered characteristic monitor transmitter 30 is coupled to a sensor set 28 by a sensor cable 32. In alternative embodiments, the cable 32 may be omitted, and the telemetered characteristic monitor transmitter 30 may include an appropriate connector for direct connection to the connector portion 27 of the sensor set 28 or the sensor set 28 may be modified to have the connector portion 27 positioned at a different location.

Figure 5:
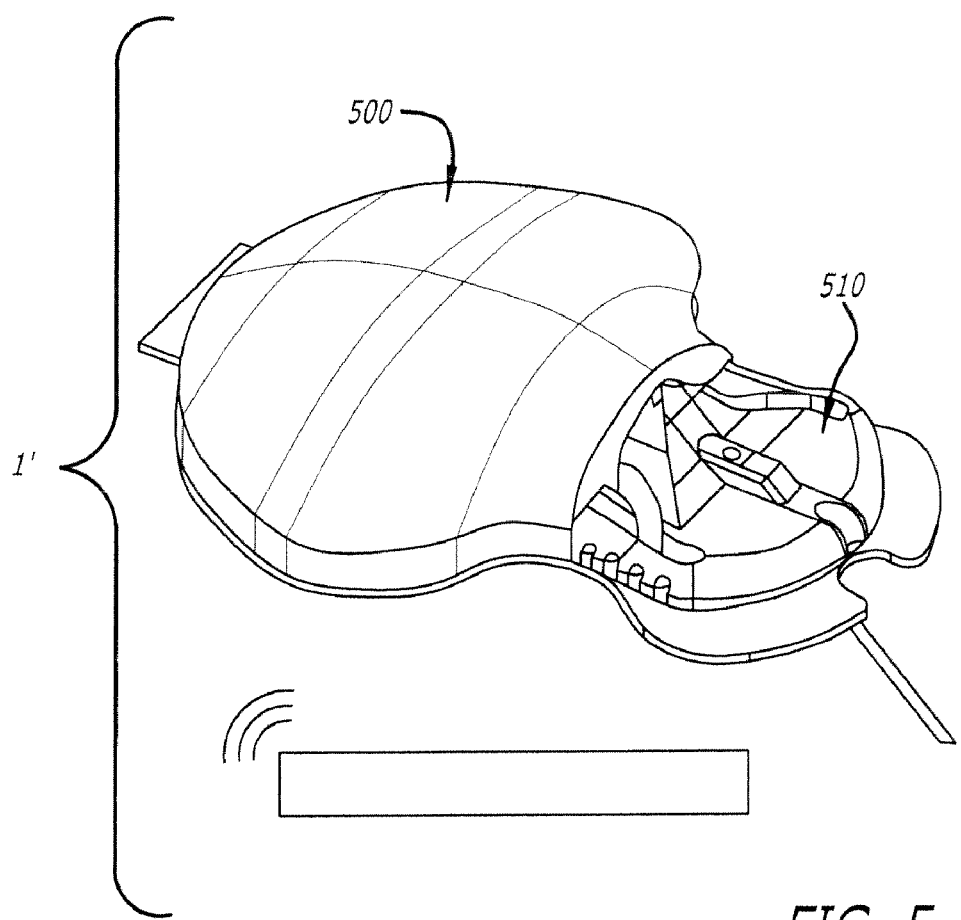
FIG. 5 is a perspective view illustrating a preferred embodiment of a subcutaneous sensor insertion set and telemetered characteristic monitor transmitter device when mated together in relation to a characteristic monitor system.
Figure 6:
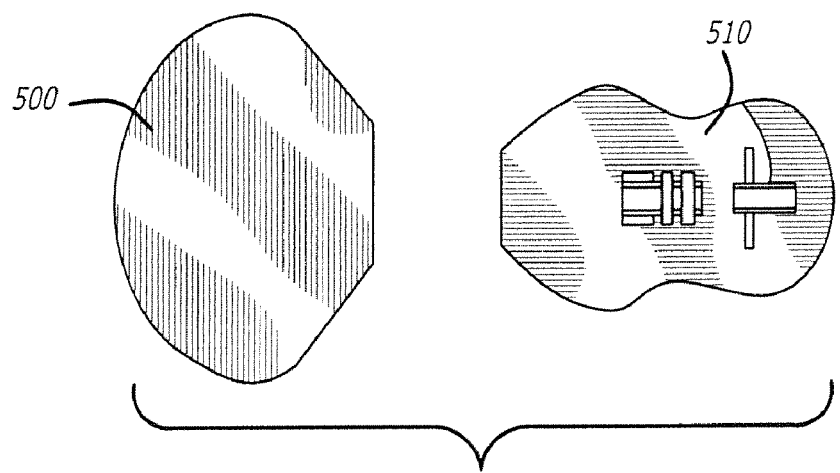
FIG. 6 is a top view of the subcutaneous sensor insertion set and telemetered characteristic monitor transmitter device when separated.

For example, FIGS. 5 and 6 show a possible alternative embodiment where characteristic monitor transmitter 500 and the sensor set 510 can be modified to allow a side-by side direct connection between the characteristic monitor transmitter 500 and the sensor set 510 such that the characteristic monitor transmitter 500 is detachable from the sensor set 510, as seen in FIG. 6. Another possible embodiment (not shown) can modify the top of the sensor set 510 to facilitate placement of the telemetered characteristic monitor transmitter 500 over the sensor set 510.

Figure 7:
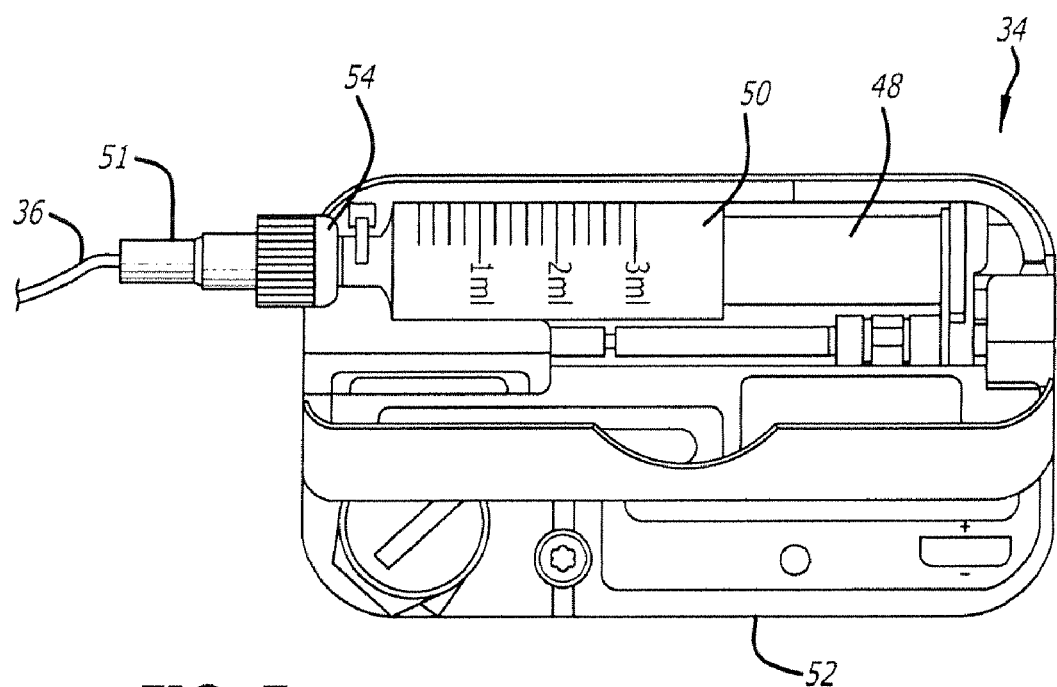
FIG. 7 is a top view of an infusion device with a reservoir door in the open position, for use in an embodiment of the present invention.
Figure 8:
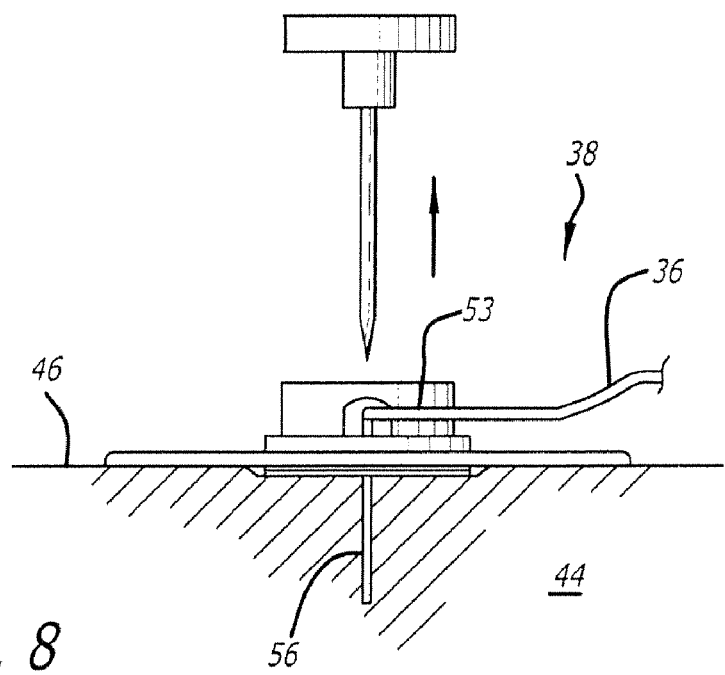
FIG. 8 is a side view of an infusion set with the insertion needle pulled out, for use in an embodiment of the present invention.

FIG. 7 is a top view of an infusion device with a reservoir door in the open position, for use in an embodiment of the present invention. Referring to FIGS. 1 and 7, the controller 12 processes the digital sensor values Dsig and generates commands 22 for the infusion pump 34. Preferably, the infusion device 34 responds to the commands 22 and actuates a plunger 48 that forces insulin 24 out of a reservoir 50 located inside the infusion device 34. In particular embodiments, a connector tip 54 of the reservoir 50 extends through the infusion device housing 52 and a first end 51 of the infusion tube 36 is attached to the connector tip 54. A second end 53 of the infusion tube 36 connects to the infusion set 38. Referring to FIGS. 2, 7 and 8, insulin 24 is forced through the infusion tube 36 into the infusion set 38 and into the body 20. The infusion set 38 is adhesively attached to the user's skin 46. As part of the infusion set 38, a cannula 56 extends through the skin 46 and terminates in the subcutaneous tissue 44 completing fluid communication between the reservoir 50 and the subcutaneous tissue 44 of the user's body 20.

In alternative embodiments, the closed-loop/semi-closed loop system can be a part of a hospital-based glucose management system. Given that insulin therapy during intensive care has been shown to dramatically improve wound healing, reduce blood stream infections, renal failure, and polyneuropathy mortality, irrespective of whether subjects previously had diabetes, the present invention can be used in this hospital setting to control the blood glucose level of a patient in intensive care.

In these alternative embodiments, since an IV hookup is typically implanted into a patient's arm while the patient is in an intensive care setting (e.g. ICU), a closed loop glucose control can be established which piggy-backs off the existing IV connection. Thus, in a hospital based system, intravenous (IV) catheters which are directly connected to a patient vascular system for purposes of quickly delivering IV fluids, can also be used to facilitate blood sampling and direct infusion of substances (e.g. insulin, anticoagulants) into the intra-vascular space. Moreover, glucose sensors may be inserted through the IV line to give real-time glucose levels from the blood stream.

Therefore, depending on the type of hospital based system, the alternative embodiments would not necessarily need the described system components, such as the sensor 26, the sensor set 28, the telemetered characteristic monitor transmitter 30, the sensor cable 32, the infusion tube 36, and the infusion set 38 as described in the preferred embodiments. Instead, standard blood glucose meters or vascular glucose sensors as described in patent application entitled "Multi-lumen Catheter," filed Dec. 30, 2002, Ser. No. 10/331,949, which is incorporated by reference herein in its entirety, can be used to provide the blood glucose values to the infusion pump control and the existing IV connection can be used to administer the insulin to the patient.

Figure 9A:
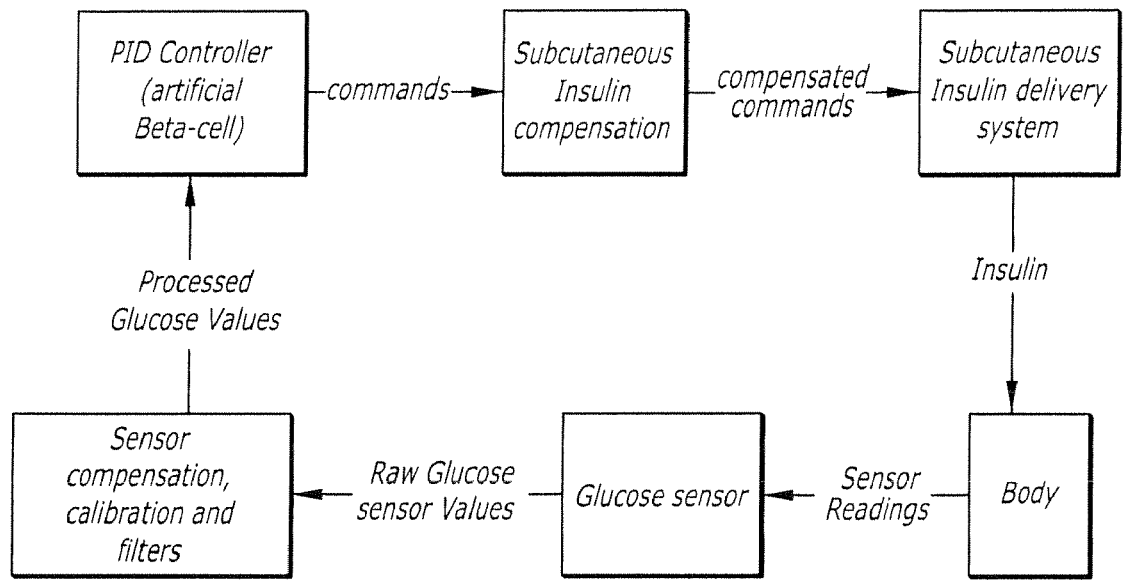
FIGS. 9(a) and 9(b) are block diagrams of a closed loop glucose control system in accordance with an embodiment of the present invention.
Figure 9B:
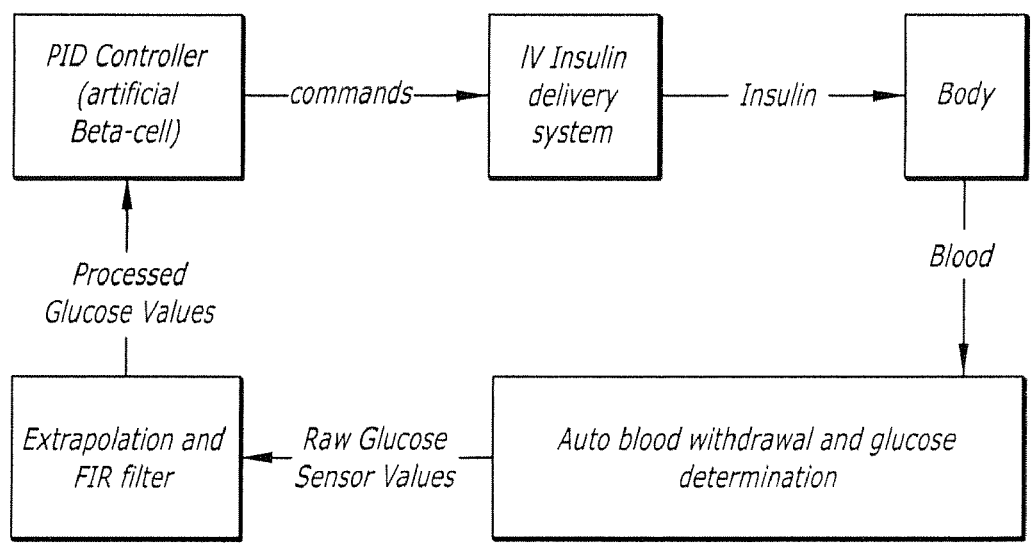

It is important to appreciate that numerous combinations of devices in the hospital-based system can be used with the closed loop controller of the present invention. FIGS. 9(a) and 9(b) illustrate examples of such combinations. Specifically, FIG. 9(a) illustrates a subcutaneous sensor system. FIG. 9(b) illustrates an auto blood glucose/intravenous insulin infusion system that can automatically withdraw and analyze blood for glucose concentration at fixed intervals (preferably 5-20 minutes), extrapolate the blood glucose values at a more frequent interval (preferably 1 minute), and use the extrapolated signal for calculating an IV-insulin infusion according to the controller described below.

The modified auto blood glucose/intravenous insulin infusion system would eliminate the need for subcutaneous sensor compensation and subcutaneous insulin compensation which would be required with a subcutaneous sensor system (as described below when discussing the delay problems inherent in a subcutaneous sensor system). The automatic withdrawal of blood, and subsequent glucose determination can be accomplished with existing technology (e.g. VIA or Biostator like blood glucose analyzer) or by the system described in FIG. 10.

Figure 10:
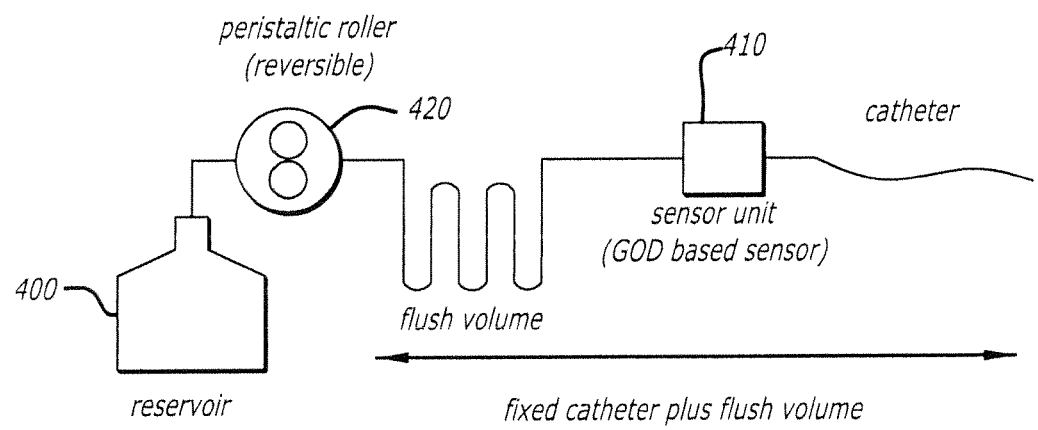
FIG. 10 is a block diagram of auto blood withdrawal and return in accordance with an embodiment of the present invention.

FIG. 10 is a block diagram of auto blood withdrawal and return in accordance with an embodiment of the present invention. The system in FIG. 10 uses a peristaltic pump 420 to withdraw blood across an amperometric sensor 410 (the same technology as used in sensor 26) and then return the blood with added flush (0.5 to 1.0 ml) from the reservoir 400. The flush may comprise of any makeup of saline, heparin, glucose solution and/or the like.

If the blood samples are obtained at intervals longer than 1 minute but less than 20 minutes, the blood glucose determinations can be extrapolated on a minute-to-minute basis with extrapolation based on the present (n) and previous values (n−1) to work with the logic of the controller as described in detail below. For blood samples obtained at intervals greater than 20 minutes, a zero-order-hold would be used for the extrapolation. Based on these blood glucose values, the infusion device can administer insulin based on the closed loop controller described in greater detail below.

In other modifications to the system, a manual blood glucose/intravenous insulin infusion system can be used where frequent manual entries of blood glucose values from a standard blood glucose meter (e.g., YSI, Beckman, etc) are extrapolated at more frequent intervals (preferably 1 min) to create a surrogate signal for calculating IV-insulin infusion. Alternatively, a sensor blood glucose/intravenous insulin infusion system can use a continuous glucose sensor (e.g., vascular, subcutaneous, etc.) for frequent blood glucose determination. Moreover, the insulin infusion can be administered subcutaneously rather than intravenously in any one of the previous examples according to the controller described below.

In still further alternative embodiments, the system components may be combined in a smaller or greater number of devices and/or the functions of each device may be allocated differently to suit the needs of the user.

Once the hardware for a closed loop/semi-closed loop system is configured, such as in the preferred embodiments described above, the affects of the hardware on a human body are determined by the controller. In preferred embodiments, the controller 12 is designed to model a pancreatic beta cell ($\beta$-cell).

In other words, the controller 12 commands the infusion device 34 to release insulin 24 into the body 20 at a rate that causes the insulin concentration in the blood to follow a similar concentration profile as would be caused by fully functioning human $\beta$-cells responding to blood glucose concentrations in the body 20. Thus, the controller 12 is intended to emulate the in vivo insulin secretion pattern and to adjust this pattern to be consistent with in vivo $\beta$-cell adaptation.

The in vivo $\beta$-cell response in subjects with normal glucose tolerance (NGT), with widely varying insulin sensitivity ($S_I$), is the optimal insulin response for the maintenance of glucose homeostasis. The biphasic insulin response of a $\beta$-cell can be modeled using components of a proportional, plus integral, plus derivative (PID) controller along with various filters. Description of a PID controller to emulate $\beta$-cells can be found in commonly assigned U.S. Pat. No. 6,558,351, which is incorporated by reference herein in its entirety.

In alternative embodiments, the controller may simply be the controller in an infusion pump that calculates the amount of insulin to be infused based upon the insulin sensitivity/carbohydrate ratio of the individual, the target blood glucose level, amount of carbohydrates to be ingested and the current blood glucose level supplied by the sensor. An example of such a controller is described in commonly assigned U.S. Pat. No. 6,554,798 entitled "External Infusion Device with Remote Programming, Bolus Estimator and/or Vibration Alarm Capabilities," which is incorporated by reference herein in its entirety. In additional embodiments, the controller may simply be a controller of an infusion pump which takes an additional input of blood glucose values from a sensor or meter, where the controller solely relies on the current glucose value (or predicted glucose value) without relying on additional factors such as insulin sensitivity or carbohydrate ratio or carbohydrates ingested. For example, the system may be used only for overnight closed-loop applications, where there is no expectation of any carbohydrates ingested. Instead, the key focus may simply be to prevent hypoglycemic excursions during sleeping times because the immediate risks of hypoglycemia are much greater than hyperglycemia. Hypoglycemia can cause a person to pass out in 15 or 30 minutes while it takes hours for the severe effects of hyperglycemia to become evident and cause problems. In such an application, the controller in the infusion pump could simply lower the basal rate or shut off the basal rate completely to prevent the blood glucose levels from falling to dangerous levels. On the other hand, the controller can also correct for hyperglycemic excursions, by increasing the basal rate simply using only insulin sensitivity factor and current blood glucose value in determining how much additional insulin to deliver.

Yet in further embodiments, the system may be a combination closed loop/open loop system. For example, a controller of an infusion pump can be programmed to go into open loop conditions during meal times (i.e. injections of meal boluses) or correction boluses, where the user will control the amount of insulin given in a bolus. However, the controller will place the system back to a default closed-loop/semi-closed system when the insulin on board from a meal or correction bolus is de minimis (for example, 2 hours).

Regardless of the controller used with the present system, closed loop/semi-closed loop algorithms for insulin delivery rely on a continuous or periodic glucose sensor to drive a control algorithm that determines the optimal insulin dose to administer through a pump delivery mechanism. Therefore, sensor reliability and fault detection and handling are crucial to the dependability and safety of such an application.

It is therefore desirable to have an assessment mechanism that can evaluate the sensor signal fidelity and initiate the appropriate action following detection of a sensor failure. In the event a fault is detected, a request for sensor replacements should be initiated and a temporary suspension of insulin delivery or control should switch to a fixed mode of operation with set basal patterns.

One method of identifying whether the sensor values are reliable involves the measure of other signals by the sensor that may provide information about the state of the sensor (such as voltage readings, impedance, etc). Another method to assure an accurate sensor reading is to use a dual or 3-up sensing system located in a single sensor site so that the sensors are used to check one another. Here, the system continues in a closed-loop mode as long as the sensors are in agreement with each other. Moreover, the likelihood of each sensor failing in the same way, or at the same time, is small.

A further method for identifying whether the sensor values are reliable relates to the use of sensor redundancy, wherein the sensing method and/or sensor location of redundant sensors are different from one another. For example, in one embodiment, two subcutaneous sensors located at different sites would assure that the potential for common effects due to sensor location or interferences is negligible.

However, alternative sites may generate different physiological delays that could result from skin temperature or pressure variance at the measuring site. For example, when additional pressure is applied to one of the sites due to sleep posture, the readings may vary. Moreover, two identical sensors that should exhibit the same readings can exhibit varying time lags, sensitivities and offsets leading to confusing signals.

Thus, in further embodiments, sensors using different technology are placed in different body fluids, e.g. one sensor in subcutaneous tissue and one in blood. Therefore, although the previous description described various types of electro-enzymatic sensors, the system will use other types of sensors, such as chemical based, optical based or the like.

For example, other types of sensors are described in the following references: U.S. Provisional Application Ser. No.

60/007,515 to Van Antwerp et al. and entitled "Minimally Invasive Chemically Amplified Optical Glucose Sensor"; U.S. Pat. No. 6,011,984 issued Jan. 4, 2000 to Van Antwerp et al. and entitled "Detection of Biological Molecules Using Chemical Amplification"; and U.S. Pat. No. 6,766,183 issued Jul. 20, 2004 to Walsh et al. and entitled "Long Wave Fluorophore Sensor Compounds and Other Fluorescent Sensor Compounds in Polymers", all of which are herein incorporated by reference. Other compounds using Donor Acceptor fluorescent techniques may be used, such as disclosed in U.S. Pat. No. 5,628,310 issued May 13, 1997 to Rao et al. and entitled "Method and Apparatus to Perform Transcutaeous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sep. 21, 1993 to Lakowicz et al. and entitled "Determination and Quantification of Saccharides by Luminescent Lifetimes and Energy Transfer", all of which are herein incorporated by reference. Hence, use of two different types of sensors at two different locations, may assure failsafe performance of the system that relies heavily on accurate sensor readings.

The insulin delivery system 14 together with the controller 12 mimics the delivery of a normal pancreas. To do so, the insulin delivery system 14 delivers steady amounts of insulin, known as a basal rate, throughout a day. The basal rate delivers the amount of insulin needed in a fasting state to maintain target glucose levels. The basal rate insulin is intended to account for the baseline insulin needs of the body, and makes up approximately fifty percent of the body's total daily insulin requirements.

Thus, similar to the pancreas, the insulin delivery system 14 delivers basal rate insulin continuously over the twenty-four hours in the day. The insulin delivery system 14 can be set to automatically provide one or more different rates during different time intervals of the day. These different basal rates at various time intervals during the day usually depend on a patient's lifestyle and insulin requirements. For example, many insulin delivery system users require a lower basal rate overnight while sleeping and a higher basal rate during the day, or users may want to lower the basal rate during the time of the day when they regularly exercise.

Figure 11:
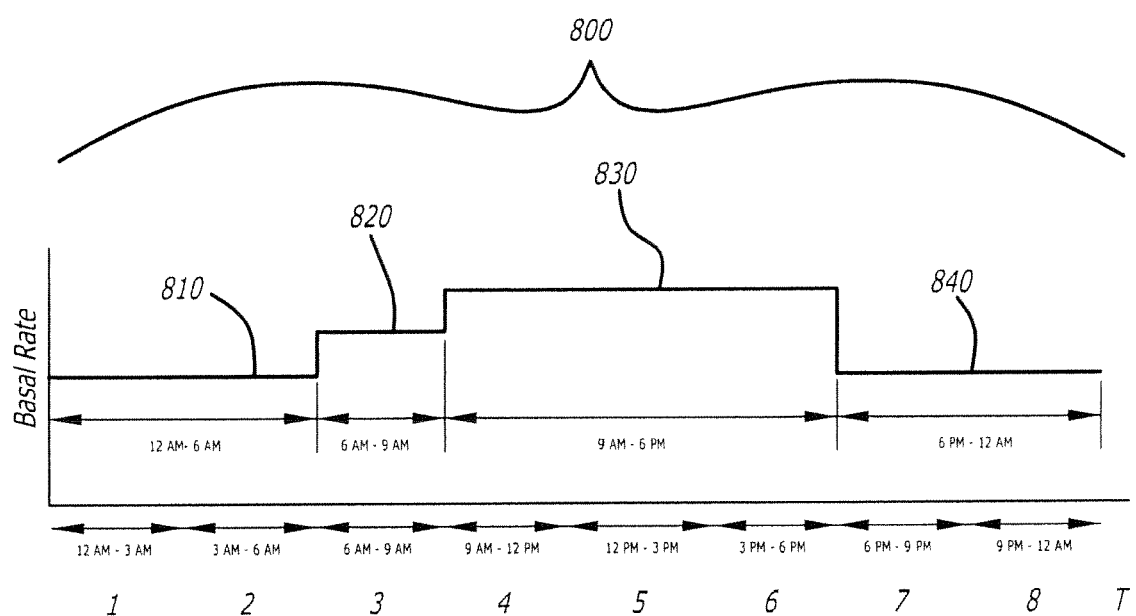
FIG. 11 is an example of a basal rate profile broken up into three-hour intervals in accordance with an embodiment of the present invention.

FIG. 11 is an example of a basal rate profile broken up into three-hour intervals in accordance with an embodiment of the present invention. Referring to FIG. 11, the basal pattern 800 can have various basal rates (810, 820, 830, 840) throughout the day, and the basal rates do not necessarily change at each interval. Moreover, adjustments to the specific basal rates can be made for each time interval. Notably, these intervals can be started at any time to match the user's schedule and intervals can be greater or less than three-hours in length. A single basal rate interval can be as short as a minimum basal rate interval capable of being programmed by an insulin delivery system or have a maximum of 24 hours.

A patient's target blood glucose level (Target) is the amount of blood glucose (BG) that the patient wishes to achieve and maintain. Typically, a target blood glucose value is between 70-120 mg/dL for preprandial BG and 100-150 mg/dL for postprandial BG. Thus, the patient's basal pattern is set to achieve and maintain the Target during insulin therapy.

According to an embodiment of the invention, an algorithm may provide intelligent therapy modifications for various pump therapy parameters to help patients more easily achieve and maintain the target blood glucose level. The algorithm automatically adjusts insulin delivery parameters based on the difference between a glycemic target and a measured glucose value.

In the preferred embodiments, the algorithm is incorporated in the controller 12 that is able to receive signals from the glucose sensor system 10. In the preferred embodiments, the algorithm is stored in the controller's firmware, but can be stored in a separate software routine in the controller's memory. In addition, the insulin delivery system 14 is able to run the algorithm to perform the necessary steps to provide intelligent therapy modifications for various pump therapy parameters.

Alternatively, the algorithm can be run on a separate device such as a PDA, smart phone, computer, or the like. In further alternative embodiments, the algorithm can be run on the glucose sensor system 10 or combination glucose sensor system/infusion delivery system or peripheral controller.

In preferred embodiments, the intelligent therapy modifications are displayed on the insulin delivery system 14, whether the modifications themselves were calculated by the controller 12 or sent from another device either by cable or wireless means. However, in alternative embodiments, the therapy recommendations can also be given on any associated device such as a glucose sensor system display, a handheld PDA, a smart phone, a computer, etc.

Considering a patient's varying body characteristics throughout the day, the patient's insulin requirements may diverge from the patient's preset basal pattern if blood glucose levels are not as expected. If so, the insulin delivery system 14 may utilize the control algorithm to determine an optimal amount of insulin to deliver to the patient. Accordingly, the controller 12 can command the insulin delivery system 14 to automatically adjust the basal rate for a given time interval according to the optimal amount determined. Hence, better therapy is provided because the patient's current insulin requirements are addressed.

However, when basal rates are allowed to be automatically changed in a closed loop and/or semi-closed loop system, the insulin delivery system 14 is susceptible to delivering too much or too little insulin to the patient if any devices involved in derivation of the adjusted basal rate fail. For example, if the sensors of the glucose sensor system 10 become faulty, then an inaccurate blood glucose level is detected. Consequently, the controller 12 may command the insulin delivery system 14 to over-deliver or under-deliver insulin to the patient. Thus, safeguards are preferably implemented to ensure against the over-delivery or under-delivery of insulin. Besides the use of multiple sensors, another (or independently used) possible safeguard may be the use of a model predictive supervisory control. A separate algorithm can be used to confirm that blood glucose values are acting as expected based on the delivery of insulin. When the actual values deviate too much from the predictive models, alarms or other corrective actions can be used. Examples of model predictive supervisory algorithms can be seen in commonly assigned U.S. patent application Ser. No. 11/700,666 entitled "Model Predictive Method and System for Controlling and Supervising Insulin Infusion" filed Jan. 31, 2007. In addition, to the above mentioned safeguards, the present invention provides for an additional (or independently used) safety mechanism to avoid over-delivery or under-delivery of insulin.

Figure 12:
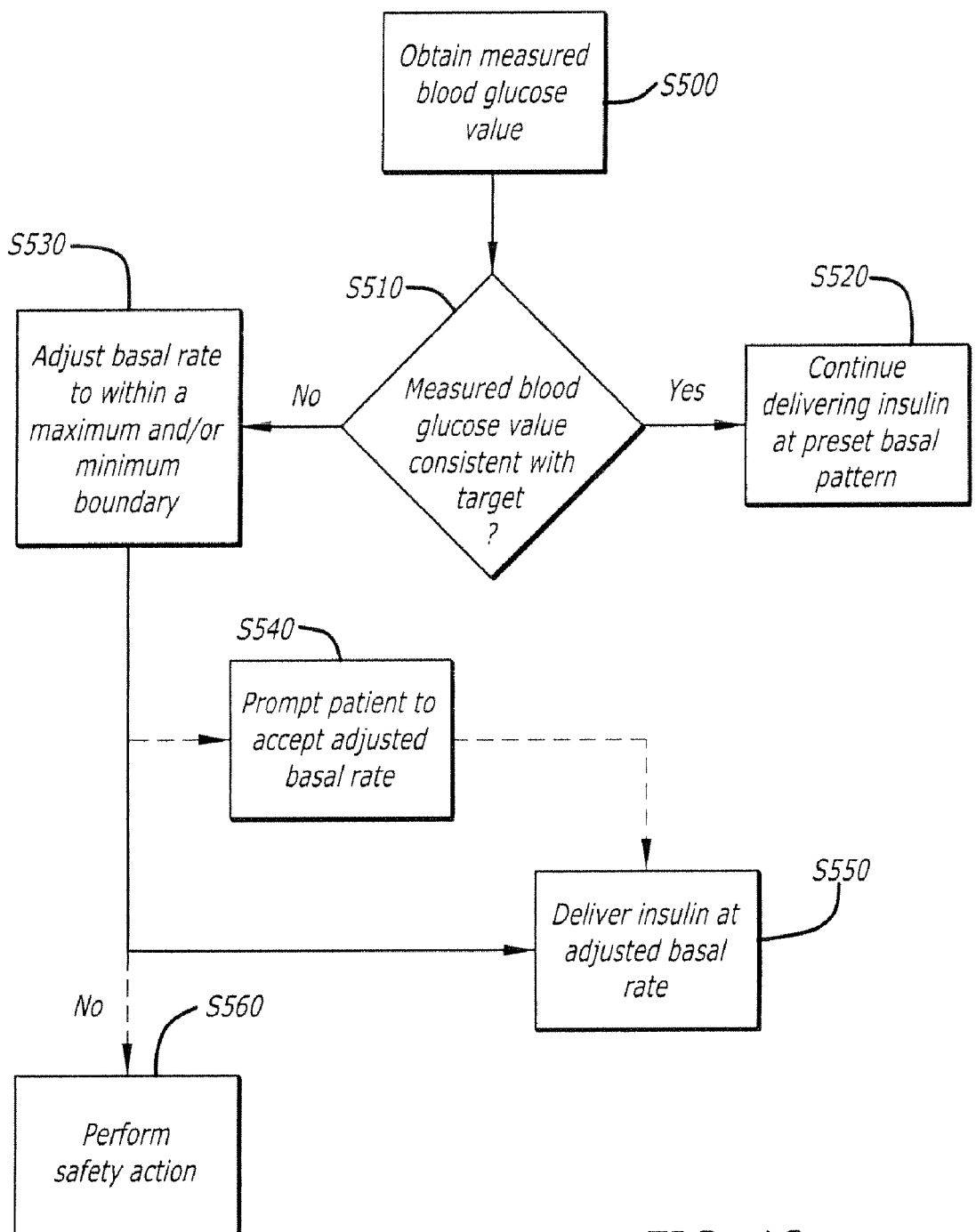
FIG. 12 is a flowchart illustrating a method for therapy modification in a closed loop/semi-closed loop infusion system in accordance with an embodiment of the present invention.

FIG. 12 illustrates a method for providing therapy modification in a closed loop/semi-closed loop infusion system, wherein the over-delivery or under-delivery of insulin is prevented in accordance with the preferred embodiments of the present invention. Referring to FIG. 12, at the end of a particular basal pattern time interval, a patient's measured blood glucose level is obtained (S500) using the glucose sensor system 10 of FIG. 1, for example.

Upon obtaining the measured blood glucose level, the controller 12 determines whether the Target is successfully achieved and maintained (S510). If so, the controller commands the insulin delivery system to continue delivering insulin to the patient according to the patient's preset personal basal pattern (S520). However, if the Target is not achieved or maintained, then the controller 12 will attempt to adjust the basal rate to a temporary adjusted basal rate (S530). Depending on whether the blood glucose is higher or lower than the targeted blood glucose level, more or less insulin will be delivered compared to the existing patient's preset basal rate set in his/her basal pattern.

However, in administering the insulin at the adjusted basal rate, the controller 12 preferably limits the adjusted basal rate to a maximum and/or minimum boundary on the adjusted basal rate (S530). The maximum and/or minimum boundary on the adjusted basal rate is set based on the preset basal rate.

For example, a predefined boundary may be set at 25% above or below the preset basal rate for any given time interval. In the preferred embodiment, 25% is chosen so that the amount of insulin makes only small changes to the blood glucose value over a longer period of time. However, this boundary can be defined at any percentage or value above or below a preset basal rate. Therefore, if the adjusted basal rate is within 25% above or below the preset basal rate, the controller 12 will command the insulin delivery system 14 to deliver insulin at the adjusted basal rate (S550). In a semi-closed system, the insulin delivery system will prompt the patient to accept the adjusted basal rate prior to the delivery of insulin (S540).

Alternatively, if the absolute value of the difference between the adjusted basal rate value and the preset basal rate value is greater than a predefined threshold (i.e. exceeds the maximum/minimum boundary on the preset basal rate), the controller 12 will only adjust the delivery rate up to the boundary value, and cap the maximum or minimum amount of adjustment allowed compared to the patient's preset basal pattern. If the preset basal pattern has programmed an increase or decrease at the next time interval (i.e. the time when the basal rate is preprogrammed to change), the maximum adjustment will move with the change in the preset basal pattern while maintaining the threshold difference between the preset basal rate and the adjusted basal rate.

Over time, if the basal rate is regularly adjusted and consistently reaches the maximum and/or minimum boundary for any given time interval, this may indicate that the patient's insulin requirements have changed, and therefore the patient's personal basal pattern may need to be altered. Accordingly, based on the maximum and/or minimum boundary value consistently reached during any given time interval, the controller 12 may recommend to the patient a new basal rate the patient can integrate into his/her personal basal pattern.

In alternative embodiments, it is contemplated that systematic errors may occur, and therefore the predefined threshold may be exceeded when adjusting the basal rate (i.e. the amount of insulin to be delivered exceeds the maximum/minimum boundary on the preset basal rate). In such a case, the controller does not automatically allow the insulin delivery system 14 to deliver insulin to the patient at the adjusted basal rate. Consequently, at least one of a number of actions will be performed (S560).

For example, the adjusted basal rate value can be evaluated for safety. In preferred embodiments, the safety review ensures that the glucose history is not too variable for a therapy modification to be made. A therapy modification should only be made if there is a consistent pattern in blood glucose levels to provide a certain level of confidence in the therapy modification.

In a preferred embodiment, real-time calibration adjustment can be performed to account for changes in sensor sensitivity during the lifespan of the glucose sensor 26 and to detect when a sensor fails. An example of real-time calibration adjustment is described in commonly assigned U.S. patent application Ser. No. 10/750,978, filed on Dec. 31, 2003, entitled "Real Time Self-Adjusting Calibration Algorithm," which is a continuation-in-part of U.S. patent application Ser. No. 10/141,375, filed on May 8, 2002, entitled "Real Time Self-Adjusting Calibration Algorithm," now U.S. Pat. No. 6,895,263, which is a continuation-in-part of U.S. patent application Ser. No. 09/511,580, filed Feb. 23, 2000, entitled "Glucose Monitor Calibration Methods," now U.S. Pat. No. 6,424,847, which are all incorporated by reference herein.

Figure 13:
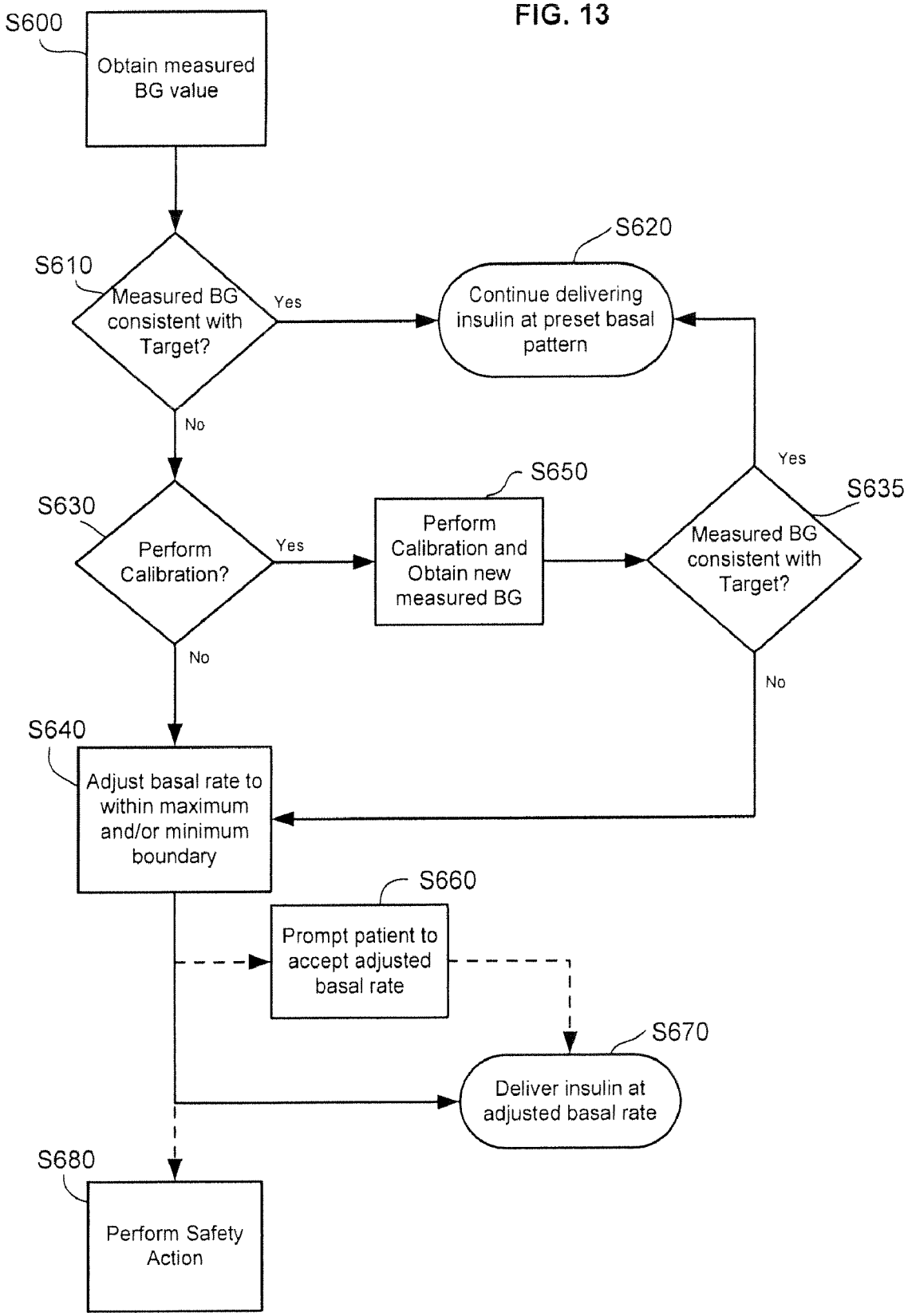
FIG. 13 is a flowchart illustrating a method for therapy modification in a closed loop/semi-closed loop infusion system implementing a self-adjusting calibration technique in accordance with an embodiment of the present invention.

FIG. 13 illustrates an additional method for providing therapy modification in a closed loop/semi-closed loop infusion system implementing real-time calibration adjustment procedures, wherein the over-delivery or under-delivery of insulin is prevented. Referring to FIG. 13, at the end of a particular basal pattern time interval (or any other time determined by the controller 12), a patient's measured blood glucose level is obtained (S600) using the glucose sensor system 10 of FIG. 1, for example.

Upon obtaining the measure blood glucose level, the controller 12 determines whether the Target is successfully achieved and maintained (S610). If so, the controller commands the insulin delivery system to continue delivering insulin to the patient according to the patient's preset personal basal pattern (S620). However, if the Target is not achieved or maintained, then the insulin delivery system must account for the possibility that (1) an inaccurate blood glucose level is detected, (2) that the sensitivity of the glucose sensor 26 is changed, or (3) the glucose sensor 26 is faulty before changing insulin delivery parameters.

In accordance with the present invention, because the closed loop/semi-closed loop infusion system implements real-time calibration adjustment procedures, the infusion system may wish to immediately calibrate the glucose sensor 26 after determining that the Target is not achieved. However, in some embodiments, the user may not wish to immediately calibrate the glucose sensor because the user may realize that the measured blood glucose values are not inaccurate. For example, if the user has recently eaten a meal, the user may expect a rise in blood glucose level because of the ingested meal. Another example is a situation where the user recently exercised and expects to see a decrease in his/her BG value. Accordingly, the blood glucose level detected by the glucose sensor system is accurate and not caused by a sensor with changed sensitivity or a faulty sensor. As a result, the user may wish to forgo calibration of the sensor and have the controller 12 immediately adjust the basal rate in order to bring the measured blood glucose level back to the Target range.

In view of the event that a rise in blood glucose level is expected and the measured blood glucose value is accurate, procedures are needed to allow the user to decide whether the immediate calibration of the glucose sensor is to be performed. In accordance with one embodiment of the present invention, if the Target is not achieved and maintained, the controller 12 will prompt the user to perform calibration of the glucose sensor (S630). If the user does not wish to perform calibration, or wishes to perform the calibration at a later time, then the controller 12 will attempt to adjust the basal rate to a temporary adjusted basal rate (S640). Depending on whether the measured blood glucose level is higher or lower than the Target, more or less insulin will be delivered compared to the existing preset basal rate set in the user's basal pattern.

If the user does wish to perform calibration, the glucose sensor system will execute calibration adjustment procedures to calibrate the glucose sensor (S650). Upon completing the calibration adjustment procedures, the user's measured blood glucose level may be obtained. The controller 12 can then determine whether the Target is successfully achieved and maintained (S635). If after completing the calibration adjustment procedures, the controller 12 determines that the calibrated measured blood glucose level is still not within the Target range (S635), the controller 12 will adjust the basal rate to a temporary adjusted basal rate (S640). As stated previously, depending on whether the measured blood glucose level is higher or lower than the Target, more or less insulin will be delivered compared to the existing preset basal rate set in the user's basal pattern. On the other hand, if after completing the calibration adjustment procedures, the controller 12 determines that the calibrated measured blood glucose level is now within the Target range (S635), the controller 12 will leave the basal rate at the preset basal pattern (S620).

In administering the insulin at the adjusted basal rate, the controller 12 preferably limits the adjusted basal rate to a maximum and/or minimum boundary on the adjusted basal rate (S640). The maximum and/or minimum boundary on the adjusted basal rate is set based on the preset basal rate.

For example, a predefined boundary may be set at 25% above or below the preset basal rate for any given time interval. In the preferred embodiment, 25% is chosen so that the amount of insulin makes only small changes to the blood glucose value over a longer period of time. However, this boundary can be defined at any percentage or value above or below a preset basal rate. Therefore, if the adjusted basal rate is within 25% above or below the preset basal rate, the controller 12 will command the insulin delivery system 14 to deliver insulin at the adjusted basal rate (S670). In a semi-closed system, the insulin delivery system will prompt the patient to accept the adjusted basal rate prior to the delivery of insulin (S660).

Alternatively, if the absolute value of the difference between the adjusted basal rate value and the preset basal rate value is greater than a predefined threshold (i.e. exceeds the maximum/minimum boundary on the preset basal rate), the controller 12 will only adjust the delivery rate up to the boundary value, and cap the maximum or minimum amount of adjustment allowed compared to the patient's preset basal pattern. If the preset basal pattern has programmed an increase or decrease at the next time interval (i.e. the time when the basal rate is preprogrammed to change), the maximum adjustment will move with the change in the preset basal pattern while maintaining the threshold difference between the preset basal rate and the adjusted basal rate.

Over time, if the basal rate is regularly adjusted and consistently reaches the maximum and/or minimum boundary for any given time interval, this may indicate that the patient's insulin requirements have changed, and therefore the patient's personal basal pattern may need to be altered. Accordingly, based on the maximum and/or minimum boundary value consistently reached during any given time interval, the controller 12 may recommend to the patient a new basal rate the patient can integrate into his/her personal basal pattern.

In alternative embodiments, it is contemplated that systematic errors may occur, and therefore the predefined threshold may be exceeded when adjusting the basal rate (i.e. the amount of insulin to be delivered exceeds the maximum/minimum boundary on the preset basal rate). In such a case, the controller does not automatically allow the insulin delivery system 14 to deliver insulin to the patient at the adjusted basal rate. Consequently, at least one of a number of actions will be performed (S680).

For example, the adjusted basal rate value can be evaluated for safety. In preferred embodiments, the safety review ensures that the glucose history is not too variable for a therapy modification to be made. A therapy modification should only be made if there is a consistent pattern in blood glucose levels to provide a certain level of confidence in the therapy modification.

In accordance with the present invention, the control algorithm may determine the variability of the glucose history by using a standard deviation of a cluster of the most recent data. The standard deviation is compared against the difference between an average blood glucose value and the target blood glucose value. If the glucose history is too variable for a therapy modification to be made, i.e. the standard deviation is greater than the difference between the average blood glucose value and the target blood glucose value, no therapy modification is made.

In alternative embodiments, the safety check is only applied for increases in the basal rate because the immediate risks of hypoglycemia are much greater than hyperglycemia. Hypoglycemia can cause a person to pass out in 15 to 30 minutes while it takes hours for the severe effects of hyperglycemia to become evident and cause problems.

In another example, if the absolute value of the difference between the adjusted basal rate value and the preset basal rate value is greater than the predefined threshold, the insulin delivery system 14 will notify the patient that the predefined threshold has been exceeded. This may be accomplished visually by informing the patient of the event through a display screen on the insulin delivery system, or by setting off different alarms via audio or vibration.

During notification, the patient may be prompted to either accept the insulin delivery at the adjusted basal rate or asked to manually input a basal rate within the predefined threshold. Additionally, during notification, the patient may be also be asked to perform a blood glucose strip meter reading to confirm whether the measured blood glucose values read by the glucose sensor system are accurate.

In preferred embodiments, all obtained and measured glucose values and basal rates adjusted during a basal pattern are logged. Accordingly, a patient can refer to the log to manage treatment more accurately. For example, the patient can utilize the log to assess where to modify the patient's personal basal pattern during a certain period of time. Moreover, as certain patterns of automatic increase and decrease of basal rates occur, the controller and the insulin delivery system can utilize the log to provide therapy recommendations to the patient for modifying the patient's personal pattern.

Figure 14:
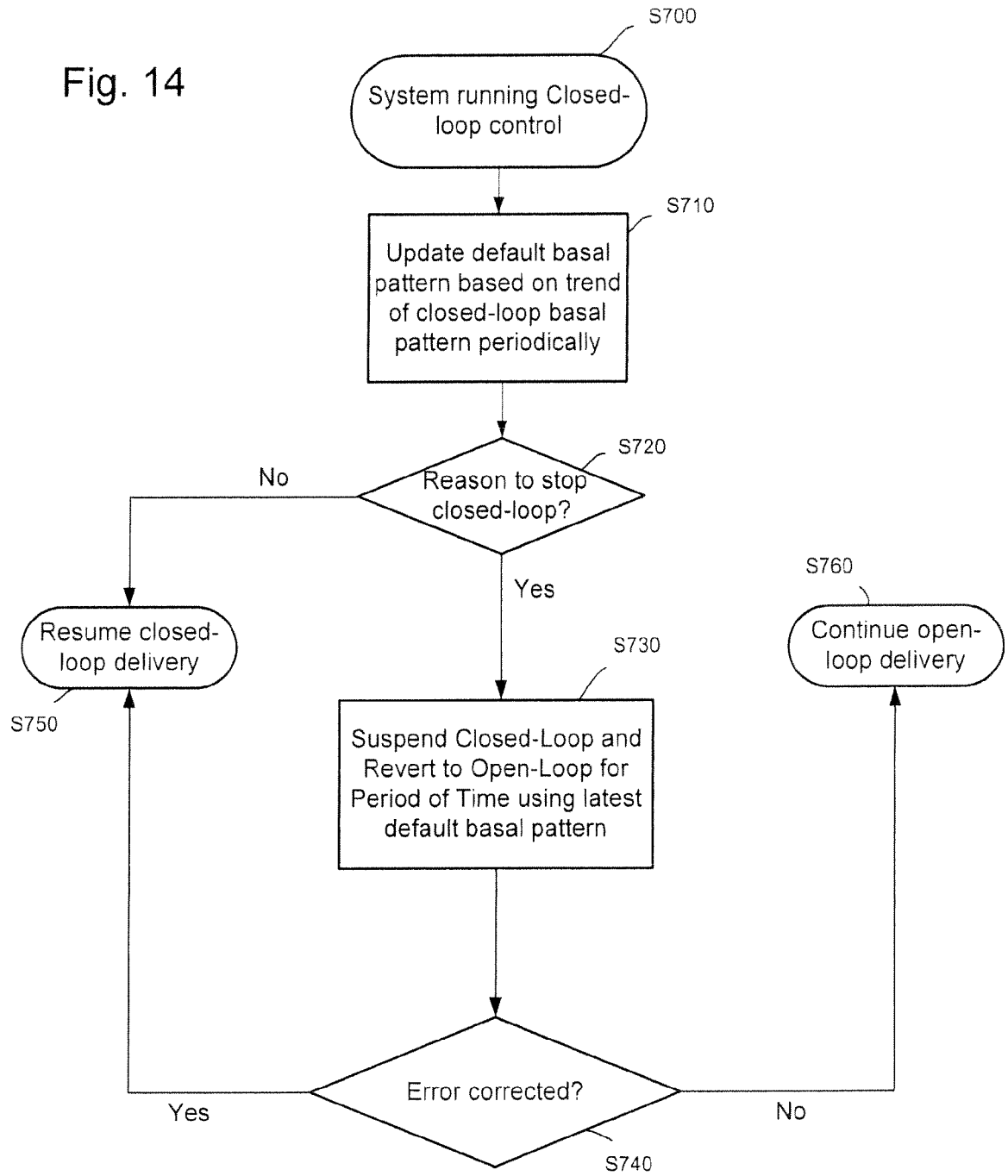
FIG. 14 is a flowchart illustrating a method for a closed loop system becoming an open-loop system where patient intervention is required in accordance with an embodiment of the present invention.

In addition to these safeguards, in preferred embodiments, there will be a safeguard that the closed-loop system will fall out of a closed-loop algorithm if certain alarms are triggered. FIG. 14 describes an embodiment of the invention where the closed-loop algorithm will turn into an open-loop system where patient intervention is required. As assumed in S700, the system is running in closed-loop mode. Thus, the delivery system is controlled automatically based on sensor readings. S710 describes that a default basal pattern can be updated periodically as the closed-loop system is run. Preferably, the default basal pattern is adjusted based on a true basal delivery history, as opposed to default preset values. Thus, the default basal patterns can be updated. Updates can be done automatically or be required to have user approval.

At S720, an event is triggered that requires the system to drop out of closed-loop control. This may be triggered by any of the previously mentioned safety features built into the closed-loop control. Since the transition from closed-loop to open-loop is itself a backup safety feature, the specific triggers can be adjusted to balance the need for safety versus unnecessarily falling out of closed-loop control. At S730, when the closed-loop control reverts into open-loop control, in preferred embodiments, the basal delivery will use the latest updated default basal patterns as described with respect to S720 to continue to deliver the necessary basal dose of insulin. However, in alternative embodiments, the open-loop system may simply revert back to the original default basal patterns. At S740, the logic returns to closed-loop control if the error has been corrected (S750) or will continue in open-loop delivery mode (S760).

In accordance with another embodiment of the present invention, the closed loop/semi-closed loop infusion system accounts for a patient's insulin on board (IOB) when providing safeguards. IOB is insulin that a patient has taken but has yet to metabolize. Generally, insulin action in the patient's body occurs slowly over time. Therefore, when a patient takes insulin via a correction bolus, for example, the correction bolus requires time to act. Accordingly, in certain circumstances, because of the delayed insulin action, the glucose sensor system may measure a high patient blood glucose level and compel the controller to deliver unneeded insulin to the patient.

To prevent "over-stacking" or the over-delivery of insulin, algorithms accounting for IOB may be programmed into the infusion system to take into consideration the delayed insulin action. Moreover, the algorithms may compare an IOB value expected as a result of a patient following normal open-loop pump therapy to an actual IOB value arising from the patient following bolus recommendations from the infusion system. Preferably, the algorithms may consider a preprogrammed tolerance, such as 50% above or below the expected IOB value, for differences between the expected IOB and the actual IOB. Preferably, as long as the actual IOB value stays within the preprogrammed tolerance (i.e. permissive IOB), the infusion system will know that insulin action is delayed, and will not trigger an alarm or automatically deliver more insulin due to an elevated glucose level in the patient.

In accordance with the present invention, because delayed insulin action causes the glucose sensor system to measure a high patient blood glucose level, the infusion system may deduce that a glucose sensor is faulty. However, by utilizing the concept of permissive IOB the delayed insulin action is taken into consideration by the infusion system, and will not alert the patient to replace the sensor unless insulin delivery becomes unreasonable. For example, a sensor would not be flagged for removal unless insulin delivery is sufficiently out of range, such as when the actual IOB value is beyond 50% above or below the expected IOB value. Conversely, even if blood glucose levels indicated by the glucose sensor seem to indicate that the current blood glucose levels are within a boundary of the targeted blood glucose, an unusual amount of insulin delivery (e.g. amount of actual IOB is much higher/lower than the expected IOB), an alarm can be triggered and/or safety procedures can be adopted as described above.

In accordance with another embodiment of the present invention, a model supervisory system may be implemented by the infusion system. The model supervisory system may use metabolic models such as a virtual patient model. Using the model, an expected glucose level can be calculated based on a past history of meals and insulin delivery and value compared to a current sensor glucose value. Similar to how a tolerance interval is placed around a permissible IOB, a tolerance interval may be placed around a model predicted glucose level. Accordingly, the supervisory model may be able to detect not only sensor error, but catheter problems as well.

While the description above refers to particular embodiments of the present invention, it will be understood that many modifications may be made without departing from the spirit thereof. Thus, the accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for providing therapy modification in an infusion system, the method comprising:
    continuously delivering insulin according to a therapy delivery parameter based on a measured blood glucose value;
    triggering an alarm based on the measured blood glucose value or an amount of insulin delivered;
    automatically adjusting the therapy delivery parameter when the alarm is triggered such that the adjusted therapy delivery parameter is limited to be within a boundary;
    comparing an expected insulin on board (IOB) value to an actual IOB value; and
    determining that insulin action is delayed if the actual IOB value is within a predetermined range of the expected IOB value,
    wherein the alarm is not triggered if it is determined that insulin action is delayed even if the measured blood glucose value is not consistent with a target blood glucose value, or the amount of insulin delivered is not consistent with an expected amount of delivered insulin.

2. The method of claim 1, further comprising selectively performing calibration of a glucose sensor system when the alarm is triggered.

3. The method of claim 1, wherein the predetermined range comprises a predetermined percentage above or below the expected IOB value.

4. The method of claim 1, wherein the alarm is not triggered if the actual IOB value is within a predetermined range of the expected IOB value.

5. The method of claim 1, wherein the alarm is triggered if the actual IOB value is not within a predetermined range of the expected IOB value.

6. The method of claim 1, wherein automatic delivery of more insulin due to an elevated glucose level is not performed if the actual IOB value is within a predetermined range of the expected IOB value.

7. The method of claim 1, wherein the therapy delivery parameter is adjusted according to a default basal pattern.

8. The method of claim 7, wherein adjusting the therapy delivery parameter comprises:
    suspending closed-loop therapy delivery; and
    reverting to open-loop therapy delivery using the default basal pattern.

9. The method of claim 8, further comprising:
resuming closed-loop therapy delivery if a condition triggering the alarm is corrected; and
continuing open-loop therapy delivery if the condition triggering the alarm is not corrected.

10. The method of claim 1, further comprising comparing the measured blood glucose value to a model predicted blood glucose value.

11. The method of claim 10, wherein the alarm is triggered if the measured blood glucose value is not within a predetermined range of the model predicted blood glucose value.

12. The method of claim 10, wherein the model predicted blood glucose value is calculated based on at least one of:
a past history of meals; and
a past history of insulin delivery and values.

13. An infusion system for providing therapy modification, the system comprising:
a glucose sensor system; and
a controller operationally connected with the glucose sensor system, wherein the controller controls a delivery system that continuously delivers insulin according to a therapy delivery parameter based on a measured blood glucose value, triggers an alarm based on the measured blood glucose value or an amount of insulin delivered, automatically adjusts the therapy delivery parameter when the alarm is triggered such that the adjusted therapy delivery parameter is limited to be within a boundary, compares an expected insulin on board (IOB) value to an actual IOB value, determines that insulin action is delayed if the actual IOB value is within a predetermined ranged of the expected IOB value so that the alarm is not triggered if it is determined that insulin action is delayed even if the measured blood glucose value is not consistent with a target blood glucose value, or the amount of insulin delivered is not consistent with an expected amount of delivered insulin.

14. The system of claim 13, wherein the controller selectively performs calibration of the glucose sensor system when the alarm is triggered.

15. The system of claim 13, wherein the predetermined range comprises a predetermined percentage above or below the expected IOB value.

16. The system of claim 13, wherein the alarm is not triggered if the actual IOB value is within a predetermined range of the expected IOB value.

17. The system of claim 13, wherein the alarm is triggered if the actual IOB value is not within a predetermined range of the expected IOB value.

18. The system of claim 13, wherein the controller does not perform automatic delivery of more insulin due to an elevated glucose level if the actual IOB value is within a predetermined range of the expected IOB value.

19. The system of claim 13, wherein the therapy delivery parameter is adjusted according to a default basal pattern.

20. The system of claim 19, wherein the controller adjusts the therapy delivery parameter by:
suspending closed-loop therapy delivery; and
reverting to open-loop therapy delivery using the default basal pattern.

21. The system of claim 20, wherein the controller:
resumes closed-loop therapy delivery if a condition triggering the alarm is corrected; and
continues open-loop therapy delivery if the condition triggering the alarm is not corrected.

22. The system of claim 13, wherein the controller compares the measured blood glucose value to a model predicted blood glucose value.

23. The system of claim 22, wherein the alarm is triggered if the measured blood glucose value is not within a predetermined range of the model predicted blood glucose value.

24. The system of claim 22, wherein the model predicted blood glucose value is calculated based on at least one of:
a past history of meals; and
a past history of insulin delivery and values.

* * * * *